(12) United States Patent
Martin et al.

(10) Patent No.: US 11,602,435 B2
(45) Date of Patent: Mar. 14, 2023

(54) JOINT ENDOPROSTHESIS MEDULLARY ROD

(71) Applicant: FX Shoulder USA Inc, Dallas, TX (US)

(72) Inventors: Baptiste Martin, Dallas, TX (US); Geoffroy Nourissat, Vincennes (FR); John Costouros, Hillsborough, CA (US); Jörg Jerosch, Meerbusch (DE); Todd Christopher Moen, Dallas, TX (US); Wayne Zealous Burkhead, Dallas, TX (US)

(73) Assignee: FX Shoulder USA Inc., Dallas, TX (US)

( * ) Notice: Subject to any disclaimer, the term of this patent is extended or adjusted under 35 U.S.C. 154(b) by 0 days.

(21) Appl. No.: 16/817,050

(22) Filed: Mar. 12, 2020

(65) Prior Publication Data

US 2020/0289279 A1    Sep. 17, 2020

(51) Int. Cl.
*A61F 2/40* (2006.01)

(52) U.S. Cl.
CPC .... *A61F 2/4059* (2013.01); *A61F 2002/4062* (2013.01)

(58) Field of Classification Search
CPC ............ A61F 2/4059; A61F 2002/4062; A61F 2002/30593; A61F 2002/30911; A61F 2002/30985; A61F 2310/00023; A61F 2/3662
See application file for complete search history.

(56) References Cited

U.S. PATENT DOCUMENTS

| | | | | |
|---|---|---|---|---|
| 5,032,134 A | * | 7/1991 | Lindwer | A61F 2/30734 623/23.36 |
| 2012/0064288 A1 | * | 3/2012 | Nakano | A61L 27/06 427/532 |

* cited by examiner

*Primary Examiner* — Bruce E Snow
(74) *Attorney, Agent, or Firm* — Troutman Pepper Hamilton Sanders LLP

(57) ABSTRACT

A medullary rod has a peripheral wall defining the outer shape of the medullary rod, and inwardly delimiting a hollow space. The medullary rod also has a plurality of first partitions. The first partitions are generally parallel to one another, extend between the inner side of the medullary rod located along the inner edge of the long bone after implantation, and the outer side of the medullary rod located along the outer edge of the long bone after implantation. Each of the first partitions is integral with the peripheral wall at these inner and outer sides of the medullary rod.

14 Claims, 9 Drawing Sheets

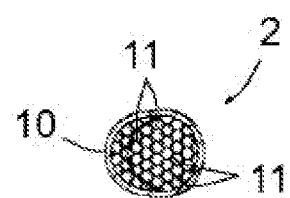
[Fig. 5]

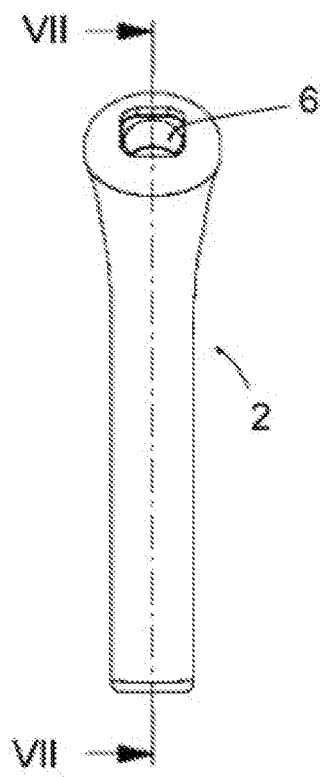

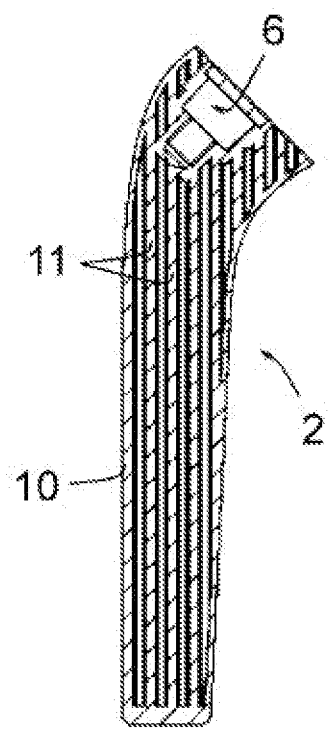
[Fig. 7]

[Fig. 8]
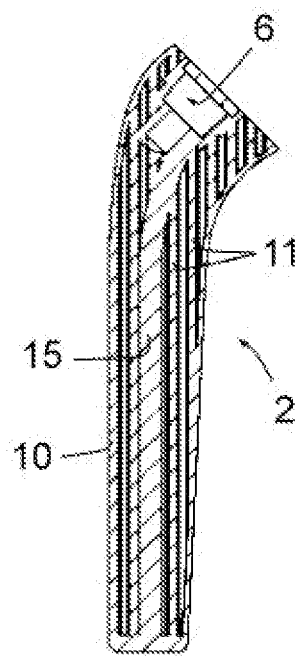

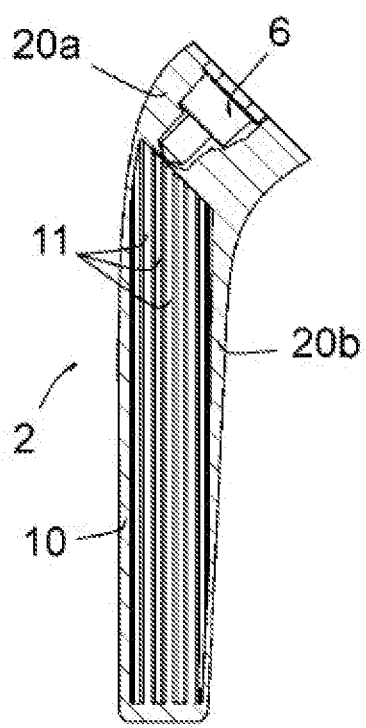

JOINT ENDOPROSTHESIS MEDULLARY ROD

CROSS-REFERENCE TO RELATED APPLICATIONS

This application claims priority under 35 U.S.C. § 119 to French patent application FR 1902534, filed January Mar. 12, 2019, the disclosure of which is incorporated herein by reference in its entirety.

TECHNICAL FIELD

The present invention relates generally to a medullary rod of a joint endoprosthesis, and, more particularly, to a joint endoprosthesis medullary rod intended to be placed in the medullary channel of a long bone of the joint in question.

BACKGROUND

It is well known to restore a joint including a long bone using a joint endoprosthesis. This endoprosthesis comprises a tapered medullary implant, intended to be placed on the long bone, by insertion thereof into the medullary channel of this bone, duly resected, and a conjugated implant, intended to be placed on the other bone making up the joint. In particular, a shoulder endoprosthesis comprises a humeral implant, intended to be placed on the long bone making up the humerus, and a glenoid implant, intended to be placed on the scapula. The humeral implant comprises a tapered medullary rod, intended to be inserted in the medullary channel of the humerus after milling and boring of the proximal part of this bone forming the medullary channel; the humeral implant also comprises a proximal part intended to be mounted on this tapered rod, which forms an articular surface. In the case of a so-called "anatomical" shoulder endoprosthesis, this proximal part may comprise a prosthetic head forming a convex articular surface, capable of cooperating with a concave conjugated articular surface; in the case of a so-called "reverse" shoulder endoprosthesis, the proximal part comprises a cavity forming a concave articular surface, which is intended to cooperate with a conjugated convex articular surface formed by the glenoid implant.

On a hip endoprosthesis, the medullary implant is a femoral rod and the conjugated implant is an acetabulum placed at the cotyloid cavity of the patient's pelvis.

A traditional medullary rod is made up of a solid and massive part, made from a metallic material, generally a titanium alloy. Such a rod is able to withstand the many and repeated forces experienced by the endoprosthesis due to movements by the patient.

However, it appears that cases of separation of the medullary rod from the bone receiving this rod are frequent. It is known that this separation is caused by the fact that the rod has a significant stiffness, much greater than that of the bone, which is a living material that is continually regenerating. Furthermore, it appears that the bone does not regenerate at certain bone parts having received the endoprosthesis because these bone parts are no longer stressed by the forces exerted on the endoprosthesis. Bone lysis can then be observed along the endoprosthesis, as well as melting of the tuberosities guaranteeing the anchoring of this endoprosthesis.

The disclosed joint endoprosthesis medullary rod aims to resolve at least this and other problems of the prior art.

SUMMARY OF THE INVENTION

To that end, the medullary rod according to some embodiments of the disclosure includes a peripheral wall, defining the outer shape of the medullary rod, and inwardly delimiting a hollow space; and a plurality of first partitions, generally parallel to one another, extending between the inner side of this medullary rod, i.e., the side that will be located along the inner edge of the long bone after implantation, and the outer side of this medullary rod, i.e., the side that will be located along the outer edge of the long bone after implantation, each of these first partitions integral with the peripheral wall at these inner and outer sides of the medullary rod.

It will be understood that the inner and outer edges of the long bone in question are the longitudinal portions of this bone that are respectively found on the inner side of the patient and on the outer side of this patient when the bone is seen from the front.

The medullary rod according at least some disclosed embodiments thus does not have a monolithic, solid and massive structure, as is the case for a traditional medullary rod made from metal, which has a structure with a peripheral wall and with a plurality of partitions inside this peripheral wall, spaced apart from one another and becoming one with said peripheral wall. This structure is particularly interesting in that it is capable of bearing the load exerted on the medullary rod due to the plurality of partitions and because these partitions become one with the peripheral wall, while having a slight deformation capacity close to that of a bone.

The peripheral wall can have a thickness of about 0.5 to 2 mm. This thickness is variable depending on the size of the medullary rod, such a rod having different sizes tailored to different patient sizes. It may be about 0.5 mm for the smallest rod in a line of medullary rods, and about 2 mm for a largest rod in this line.

Each partition may have a thickness of about 0.5 to 1.5 mm. The space between the partitions can be from about 1 to 2 mm. These dimensions are also variable depending on the size of the medullary rod, such a rod having different sizes tailored to different patient sizes.

The number of partitions can be from 4 to 6 partitions on a medullary rod intended for a small patient, and from six to ten partitions on a medullary rod intended for a large patient.

The partitions can be planar or can have an undulating profile.

The medullary rod can also comprise a plurality of second partitions, generally parallel to one another, having a different orientation from that of said first partitions and thus intersecting these first partitions, each of said second partitions integral with the peripheral wall of the medullary rod and integral with said first partitions.

The set of first and second partitions thus has a crisscrossed structure as seen in cross-section.

Said first partitions can have a purely inner-outer orientation, i.e., they can extend parallel to a frontal plane of the patient; these first partitions, and second partitions as cited above, can also extend along non-right angles relative to this frontal plane; the angles formed by the first partitions relative to this frontal plane can be equal to the angles formed by the second partitions relative to this same frontal plane, such that the first and second partitions are arranged in a crossbuck pattern relative to this frontal plane.

Said second partitions make it possible to optimize the resistance of the endoprosthesis to the repeated stresses that such an endoprosthesis is intended to experience, while having a slight deformation capacity corresponding to the Young's modulus of the bone, therefore limiting the risk of separation of the endoprosthesis from this bone.

The cells delimited by said first and second partitions may have a substantially circular, octagonal, triangular or square cross-section, depending on the shape and/or orientation of said partitions relative to one another.

Alternatively, said first partitions and second partitions delimit cells between them having a honeycomb structure.

Such a medullary rod has been found to have the optimal performance levels to obtain the desired result, namely providing an endoprosthesis that is strong and has a slight degree of resilient deformability, close to that of a bone.

The medullary rod may have a longitudinal inner structure, with a solid cross-section, integral with the peripheral wall and said first partitions and second partitions when these second partitions are present.

This structure allows longitudinal reinforcement of the rod.

In particular, this inner structure can be in the form of a central inner bar extending longitudinally between the distal end of the rod, or a zone of this rod close to this distal end, and the proximal end of the rod, or a zone close to this proximal end. This bar can be rectilinear between these ends or these zones, or it can be curved at its proximal portion so as to follow a curved shape that the medullary rod may have at the proximal level.

Said inner structure can also be in the form of a solid proximal portion connected to a longitudinal portion extending along the inner edge of the rod. This longitudinal portion can have a constant cross-section can have a cross-section becoming smaller in the distal direction, such that the longitudinal portion has a tapered shape as seen in the frontal plane.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures:

FIG. 5 is a view of the medullary rod in sectional view in plane V-V of FIG. 2;

FIG. 6 is a view of the medullary rod of the implant according to a second embodiment, in the sagittal plane, as seen from the inner side of this rod;

FIG. 7 is a view of the rod in section al view in plane VII-VII of FIG. 6;

FIG. 8 is a view of the rod similar to FIG. 7, according to a third embodiment; and FIG. 9 is a view of the rod similar to FIG. 7, according to a fourth embodiment.

DETAILED DESCRIPTION

Figure 1:
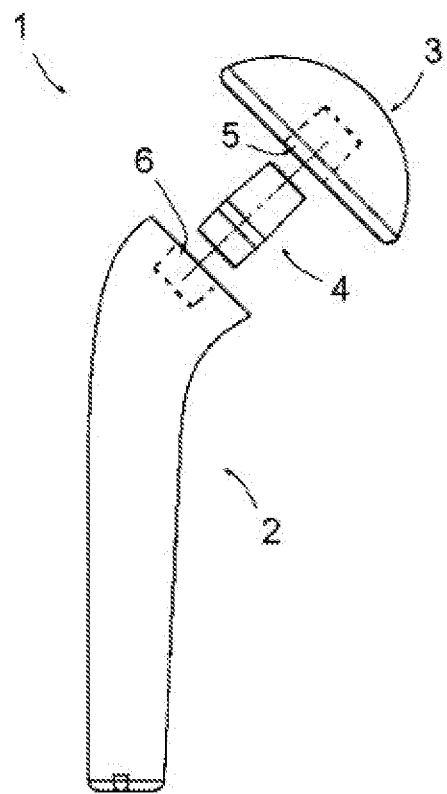
FIG. 1 is a view of the humeral implant of a prosthetic shoulder, in the frontal plane, according to a first embodiment, three components of this implant being shown in exploded view.
Figure 2:
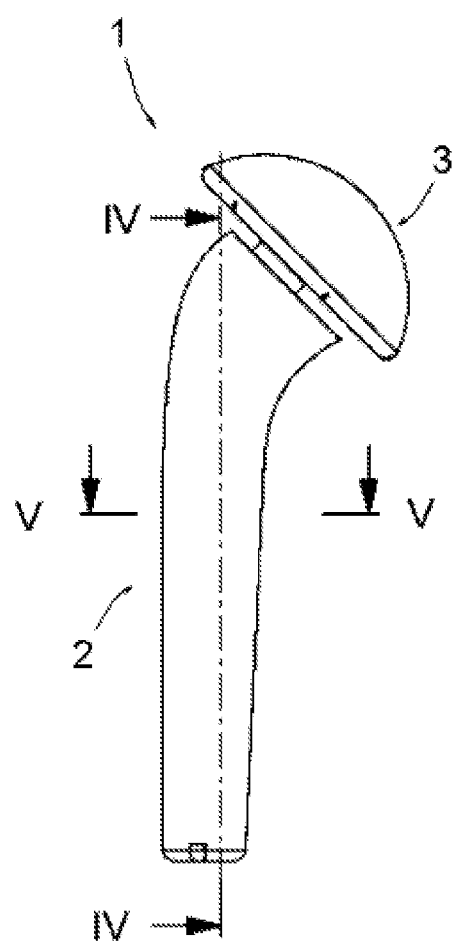
FIG. 2 is a view of the implant similar to FIG. 1, the three components being in an assembled state.
Figure 3:
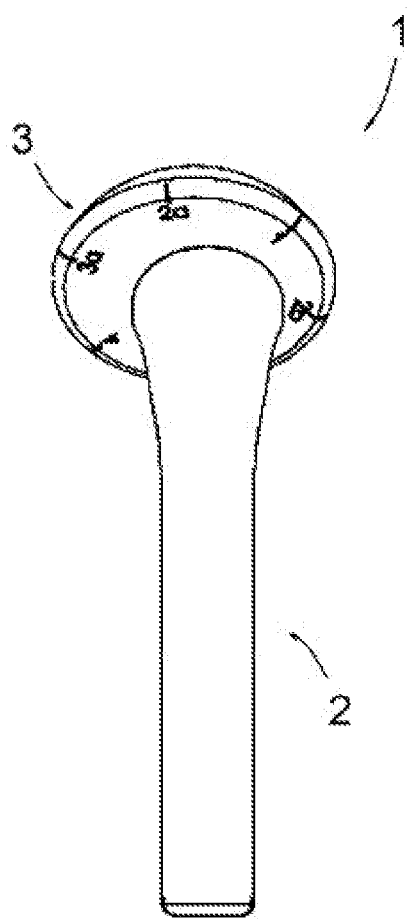
FIG. 3 is a view of the implant in the sagittal plane, as seen from the outer side of this implant.

FIGS. 1 to 3 show the humeral implant 1 of a joint endoprosthesis of the shoulder, comprising a medullary rod 2, an articulation head 3 and a neck 4 joining this head to this rod. The endoprosthesis also comprises a glenoid implant intended to be placed on the scapula of the patient and is not described herein.

The articulation head 3 is, in the illustrated example, of the so-called "anatomical" type, i.e., forming a convex articular surface capable of cooperating with a concave conjugated articular surface formed by the glenoid implant. This head is of the traditional type, in particular made from metal, and comprises a slightly conical cavity 5 for receiving, via a pressure fit, a corresponding slightly conical endpiece formed by the neck 4. Also in the illustrated example, and as shown in FIG. 3, the cavity 5 is off-centered relative to the head 3 so as to make it possible to vary the position of the head 3 relative to the rod 2 depending on the angular placement of this head on the endpiece 4, so as to make it possible to obtain an optimal fit of the humeral implant 1 to the specific anatomy of the patient. To make it possible to identify the angular position of the head 3 relative to the rod 2, the face of this head facing this rod is graduated at the periphery of this face.

The neck 4 is of the traditional type, in particular made from metal; aside from the aforementioned endpiece for assembly to the head 3, it comprises, opposite this first endpiece, a counterpart endpiece for its assembly to the rod 2, the latter comprising a cavity 6 with a shape suitable for receiving the said second endpiece with jamming.

The medullary rod 2 has a shape suitable for insertion in the medullary channel of a humerus, after cutting the proximal part of this humerus and appropriate boring of the medullary channel of the bone.

Figure 4:
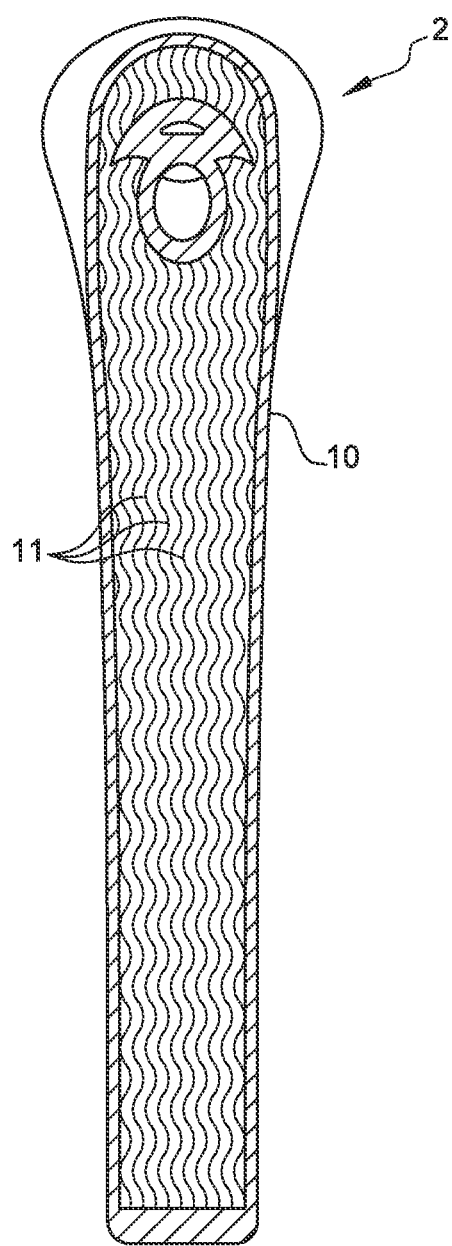
FIG. 4 is a view of a medullary rod comprised by the implant, in sectional view in plane IV-IV of FIG. 2.

As visible in FIGS. 4 and 5, the rod 2 has a peripheral wall 10, defining the outer shape of this rod, and a plurality of partitions 11 defining a honeycomb structure, these partitions 11 filling all of the hollow space inwardly delimited by this wall 10, with the exception of a proximal solid part delimiting the cavity 6.

The partitions 11 form a body with the wall 10, the entire rod 2 being made by a manufacturing method called "3D printing" or "additive" manufacturing, known in itself, by which the object to be manufactured is made by building up successive layers of hardenable material; this material is hardened in specific locations of each layer, intended to form a layer of the object to be obtained, and is in particular polymerized using a laser.

Some of the partitions 11 that delimit the honeycomb cells are oriented in an inner-outer direction of the rod 2, i.e., along a left-right direction in FIG. 5, while the other partitions 11 are oriented in an anterior-posterior direction, i.e., in a top-bottom direction in FIG. 5. The longitudinal axes of the cells delimited by the partitions 11 are also parallel to the longitudinal axis of the medullary rod 2 in the illustrated example embodiment.

It will be understood that the expression "inner-outer direction" refers to a direction going from the edge of this medullary rod intended to be located along the inner edge of the humerus after implantation, to the opposite edge intended to be located along the outer edge of the humerus after implantation; similarly, the expression "anterior-posterior direction" refers to the direction going from the edge of the rod 2 intended to be located along the anterior edge of the humerus after implantation to the edge of this rod located along the posterior edge of the humerus after implantation.

The medullary rod 2 thus has a structure with a peripheral wall 10 and a plurality of partitions 11 having inner-outer and anterior-posterior orientations, spaced apart from one another and being integral with said peripheral wall 10. This structure is particularly interesting in that it is capable of supporting the load exerted on the medullary rod 2 due to the plurality of partitions 11 and the fact that these partitions are integral with the peripheral wall 10, while having a slight deformation capacity close to that of a humerus.

FIGS. 6 and 7 show a medullary rod 2 according to a second embodiment, in which said inner-outer and anterior-posterior partitions 11 do not have undulations like those delimiting the cells according to the first embodiment, but are, on the contrary, planar and intersect one another at right angles, the inner structure formed by these partitions thus being "crisscrossed".

FIG. 8 shows a medullary rod 2 according to a third embodiment, in which the rod 2 has a solid inner bar 15, extending between the distal end wall of the rod 2 and at least one wall delimiting the cavity 6. This bar 15 is integral with the peripheral wall 10 and the partitions and is made from the same material as these walls 10 and partitions 11; it can have any appropriate cross-section, in particular a circular cross-section; its size in the inner-outer direction can in particular represent, about a third of the inner-outer dimension of the medullary rod at its tapered distal portion as shown in FIG. 8.

The bar 15 allows localized longitudinal reinforcement of the rod 2.

FIG. 9 shows a medullary rod 2 according to a fourth embodiment, in which said hollow space occupied by the partitions 11 does not extend over the entire space delimited by the peripheral wall 10. Indeed, the rod 2 has a solid part, made from the same material as the wall 10 and the partitions 11, located along at least one edge of the peripheral wall 10. In the illustrated example, this solid part comprises a portion 20a extending over a proximal part of the rod, around the cavity 6 and a portion 20b extending over a proximal part of the longitudinal edge of the rod 2 intended to be located along the inner edge of the humerus after implantation, this portion 20b becoming smaller in cross-section in the distal direction, such that the portion 20 has a tapered shape as seen in the frontal plane as in FIG. 9.

This solid part, like the bar 15, also allows a localized longitudinal reinforcement of the rod 2.

The elements of the figures are not exclusive. Other embodiments may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention

The invention claimed is:

1. A medullary rod of a joint endoprosthesis for placement in the medullary channel of a long bone comprised by the joint in question, comprising:
    a peripheral wall, defining the outer shape of the medullary rod, and inwardly delimiting a hollow space; and
    a plurality of first partitions, having an undulating profile and generally parallel to one another, extending between an inner side of the medullary rod located along the inner edge of the long bone after implantation, and an outer side of the medullary rod located along the outer edge of the long bone after implantation, each of these first partitions being integral with the peripheral wall at the inner and outer sides of the medullary rod.

2. The medullary rod according to claim 1, wherein the peripheral wall has a thickness of about 0.5 to 2 mm.

3. The medullary rod according to claim 1, wherein each partition has a thickness of about 0.5 to 1.5 mm.

4. The medullary rod according to claim 1, wherein in a space between the partitions is from about 1 to 2 mm.

5. The medullary rod according to claim 1, wherein the number of partitions is from 4 to 6 partitions on a medullary rod intended for a small patient and from six to ten partitions on a medullary rod intended for a large patient.

6. The medullary rod according to claim 1, wherein the partitions are planar.

7. The medullary rod according to claim 1, further comprising a plurality of second partitions, generally parallel to one another, having a different orientation from that of said first partitions and intersecting the first partitions, each of said second partitions being integral with the peripheral wall of the medullary rod and being integral with said first partitions.

8. The medullary rod according to claim 7, wherein said first partitions and second partitions delimit cells between them having a honeycomb structure.

9. The medullary rod according to claim 7, further comprising a longitudinal inner structure, with a solid cross-section, being integral with the peripheral wall and said first partitions and second partitions.

10. The medullary rod according to claim 9, wherein said inner structure is in the form of a central inner bar extending longitudinally between the distal end of the rod, or a zone of this rod close to this distal end, and the proximal end of the rod, or a zone close to this proximal end.

11. The medullary rod according to claim 9, wherein said inner structure is in the form of a solid proximal portion connected to a longitudinal portion extending along the inner edge of the rod.

12. The medullary rod according to claim 1, further comprising a longitudinal inner structure, with a solid cross-section, being integral with the peripheral wall and said first partitions.

13. The medullary rod according to claim 12, wherein said inner structure is in the form of a central inner bar extending longitudinally between the distal end of the rod, or a zone of this rod close to this distal end, and the proximal end of the rod, or a zone close to this proximal end.

14. The medullary rod according to claim 12, wherein said inner structure is in the form of a solid proximal portion connected to a longitudinal portion extending along the inner edge of the rod.

* * * * *